(12) United States Patent
Kawamura et al.

(10) Patent No.: US 8,509,868 B2
(45) Date of Patent: Aug. 13, 2013

(54) METHOD FOR MEASURING A CONCENTRATION OF A BIOGENIC SUBSTANCE CONTAINED IN A LIVING BODY

(75) Inventors: Tatsurou Kawamura, Kyoto (JP); Masaru Minamiguchi, Kyoto (JP); Masahiko Shioi, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/483,756

(22) Filed: May 30, 2012

(65) Prior Publication Data

US 2012/0265038 A1    Oct. 18, 2012

Related U.S. Application Data

(63) Continuation of application No. PCT/JP2011/006714, filed on Nov. 30, 2011.

(30) Foreign Application Priority Data

Apr. 12, 2011 (JP) ................................ 2011-087873

(51) Int. Cl.
*A61B 5/1455* (2006.01)
(52) U.S. Cl.
USPC ............................................ 600/316; 600/310
(58) Field of Classification Search
USPC ......................................... 600/310, 316, 322
See application file for complete search history.

(56) References Cited

U.S. PATENT DOCUMENTS

| | | | |
|---|---|---|---|
| 2005/0027176 A1* | 2/2005 | Xie | 600/316 |
| 2008/0214913 A1* | 9/2008 | Van Gogh et al. | 600/318 |
| 2009/0118605 A1* | 5/2009 | Van Duyne et al. | 600/365 |
| 2010/0195106 A1 | 8/2010 | Ogawa | |
| 2010/0309466 A1 | 12/2010 | Lucassen et al. | |

FOREIGN PATENT DOCUMENTS

| | | |
|---|---|---|
| JP | 2004-510527 | 4/2004 |
| JP | 2007-537805 | 12/2007 |
| JP | 2008-531989 | 8/2008 |
| JP | 2008-537141 | 9/2008 |
| JP | 2010-501252 | 1/2010 |
| WO | WO 02/30275 A1 | 4/2002 |
| WO | WO 2005/110207 A1 | 11/2005 |
| WO | WO 2008/024288 A2 | 2/2008 |

OTHER PUBLICATIONS

International Search Report issued in International Patent Application No. PCT/JP2011/006714 dated Dec. 27, 2011.
M.F. Mrozek et al., "Detection and Identification of Aqueous Saccharides by Using Surface-Enhanced Raman Spectroscopy," Analytical Chemistry, vol. 74, No. 16, 4069-4075, 2002.

* cited by examiner

*Primary Examiner* — Eric Winakur
(74) *Attorney, Agent, or Firm* — McDermott Will & Emery LLP

(57) ABSTRACT

One of the purposes of the present invention is to provide a biogenic substance concentration measuring method with improved measuring accuracy. An embodiment of the present invention provides a method for measuring a concentration of a biogenic substance contained in a living body, the method comprises steps of preparing a measuring device, wherein the measuring device comprises a light source, an optical filter, and a light receiver; irradiating different focused lights from the light source onto a particle chip implanted in a skin though a position on the surface of the skin to generate corresponding reflected lights; calculating the concentration of the biogenic substance on the basis of the difference of signals obtained from the reflected lights.

5 Claims, 12 Drawing Sheets

Fig. 5
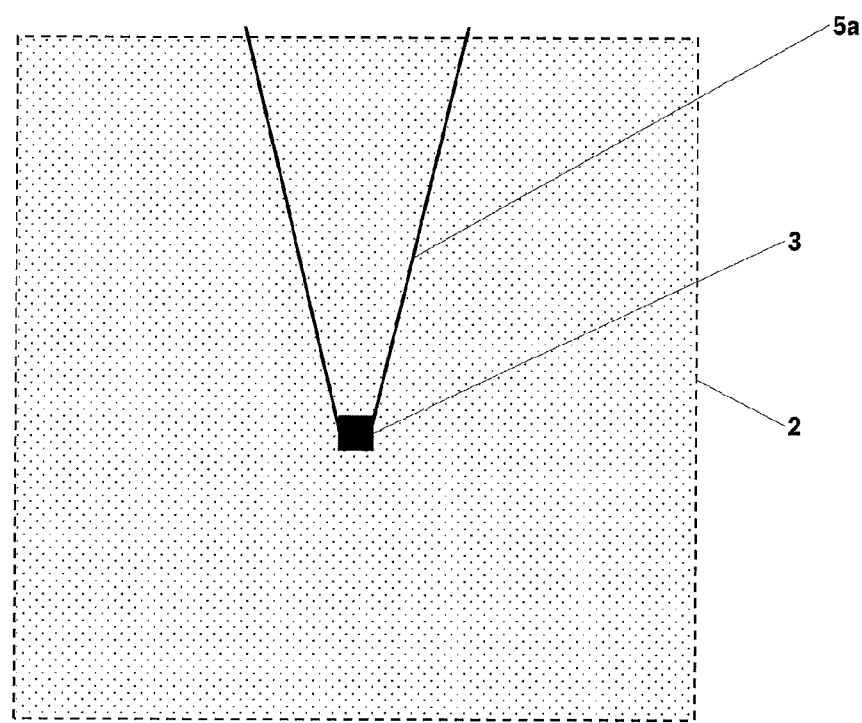
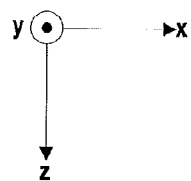

Fig. 6
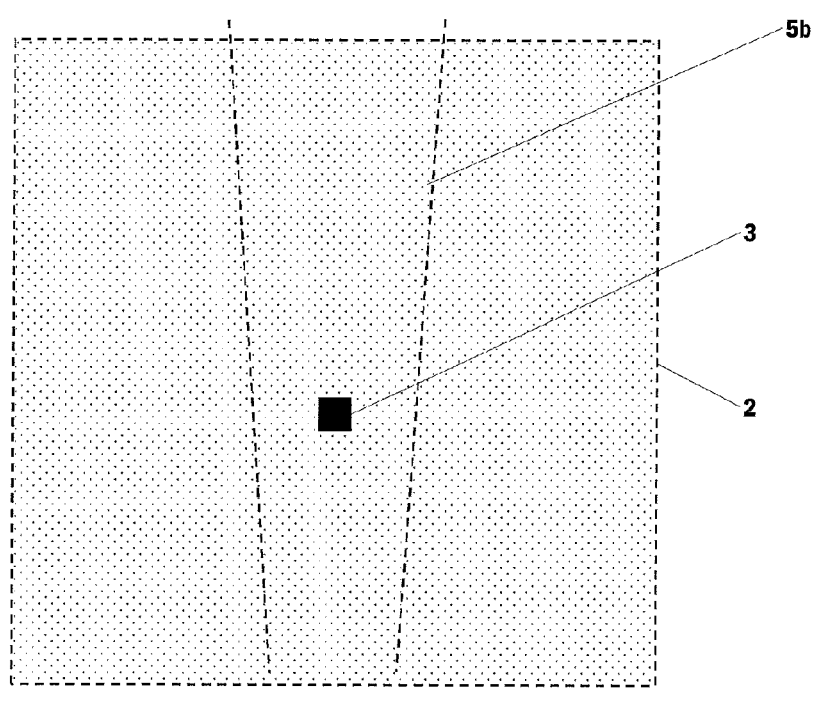
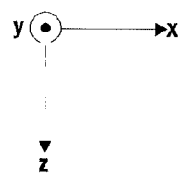

Fig. 7
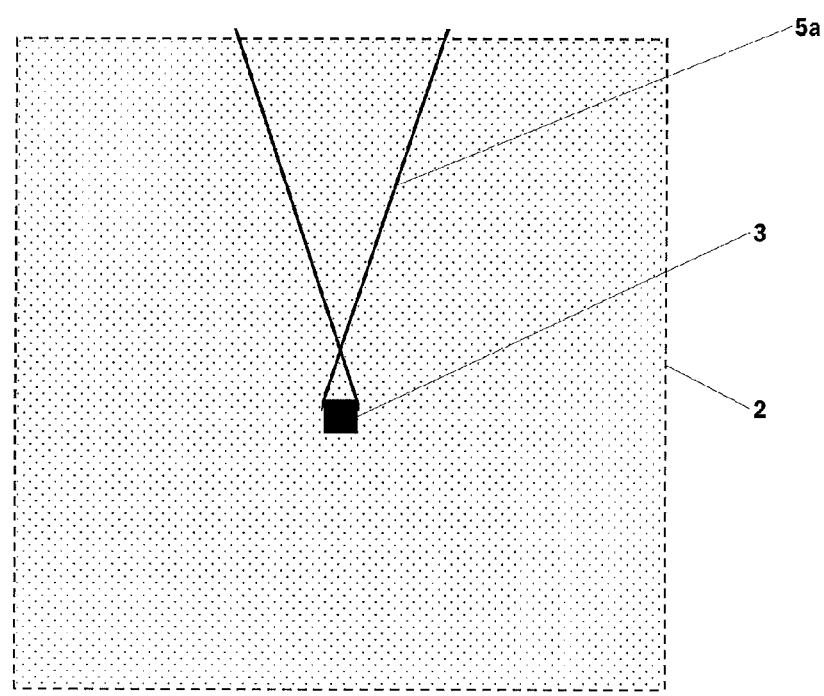
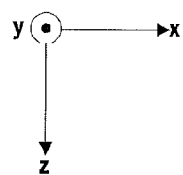

Fig. 8
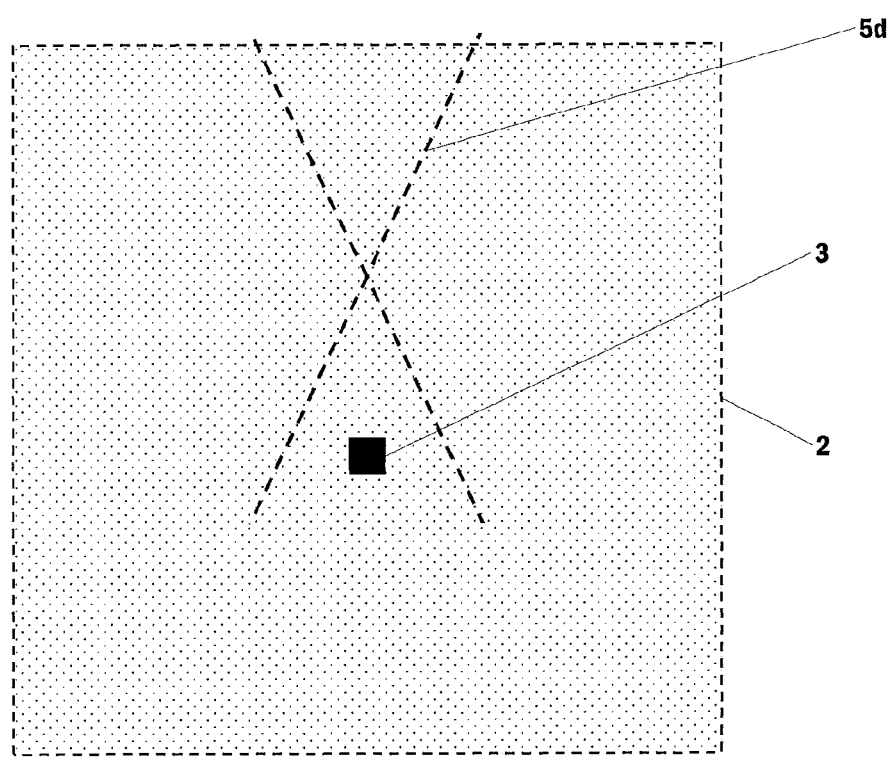
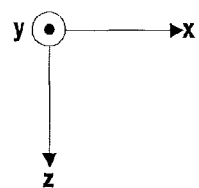

METHOD FOR MEASURING A CONCENTRATION OF A BIOGENIC SUBSTANCE CONTAINED IN A LIVING BODY

RELATED APPLICATIONS

This is a continuation of PCT International Application PCT/JP2011/006714 filed on Nov. 30, 2011, which claims priority to Japanese Patent Application No. 2011-087873 filed on Apr. 12, 2011. The disclosures of these applications including the specifications, the drawings, and the claims are hereby incorporated by reference in their entirety.

TECHNICAL FIELD

The present invention relates to a method for measuring a concentration of a biogenic substance such as glucose contained in a living body.

BACKGROUND ART

A concentration of a biogenic substance such as glucose contained in a living body is measured on the basis of reflected light, scattered light, or transmitted light of light irradiated on the living body. More particularly, Raman scattering light of the biogenic substance is observed, and the concentration of the biogenic substance is calculated on the basis of the intensity of the Raman scattering light.

Patent Literature 1 and 2 disclose a method for measuring a glucose concentration optically. According to the method, first, a particle is implanted in the upper layer of a skin. The particle contains a reagent to react with glucose and to change a fluorescence property thereof. Next, the particle is irradiated with light having an exciting wavelength from the outside of the living body so as to measure fluorescence generated at the particle through the skin. On the basis of the measured fluorescence, the glucose concentration is measured.

CITATION LIST

Patent Literature

[PLT1]
Japanese Unexamined patent Application Publication (Translation of PCT Application) No. 2004-510527.
[PLT2]
Japanese Unexamined patent Application Publication (Translation of PCT Application) No. 2007-537805.

Non Patent Literature

[Non Patent Literature 1]
Melissa F. Mrozek, and Michael J. Weaver, "Detection and Identification of Aqueous Saccharides by Using Surface-Enhanced Raman Spectroscopy", Analytical Chemistry, Vol. 74, No. 16, 4069-4075, 2002

SUMMARY OF INVENTION

Technical Problem

One of the purposes of the present invention is to provide a method for measuring a concentration of a biogenic substance contained in a living body more accurately.

Solution to Problem

[1] A method for measuring a concentration of a biogenic substance contained in a living body, the method comprising steps of:
a step (a) of preparing a measuring device comprising a light source, a focusing controller, an optical filter, and a light receiver;
a step (b) of transmitting a first focused light from the light source through the focusing controller, and focusing the first focused light on a surface of a particle chip implanted in a skin though a first area on the surface of the skin so as to generate a first reflected light, wherein
the particle chip comprises a substrate and a plurality of metal particles,
a step (c) of receiving the first reflected light by the light receiver through the optical filter to obtain a first signal Xa, the following equation (III) is satisfied:

$$\lambda_2 = (10^7 * \lambda_1) / (10^7 - B * \lambda_1) \quad \text{(III)}.$$

$\lambda_2$: the central wavelength of optical filter,
$\lambda_1$: the wavelength of the first focused light,
B: Raman shift of the biogenic substance;
a step (d) of transmitting a second focused light from the light source through the focusing controller, and irradiating the surface of the particle chip with the second focused light through a second area on the surface of the skin so as to generate a second reflected light, wherein
the focal point of the second focused light is different from the focal point of the first focused light,
the first area is identical to the second area, and
a step (e) of receiving the second reflected light by the light receiver through the optical filter to obtain a second signal Xb,
a step (f) of calculating the concentration of the biogenic substance on the basis of the difference between the first signal Xa and the second signal Xb.
[2]. A method according to item 1, wherein, the biogenic substance is glucose, and B is 1120 cm$^{-1}$.
[3]. A method according to item 1, wherein, the steps (b) and (c) are performed at the same time.
[4]. A method according to item 1, wherein, the steps (d) and (e) are performed at the same time.
[5]. A method according to item 1, wherein, the steps (d) to (f) are performed at the same time.

Advantageous Effects of Invention

An embodiment of the present invention provides a method for more accurately measuring a concentration of a biogenic substance contained in a living body.

BRIEF DESCRIPTION OF DRAWINGS

FIG. 5 shows a first focused light 5*a*.
FIG. 6 shows a second focusing light 5*b*.
FIG. 7 shows another example of the first focused light 5*a*.
FIG. 8 shows another example of the second focused light 5*b*.

DESCRIPTION OF EMBODIMENTS

Embodiment 1

Figure 1:
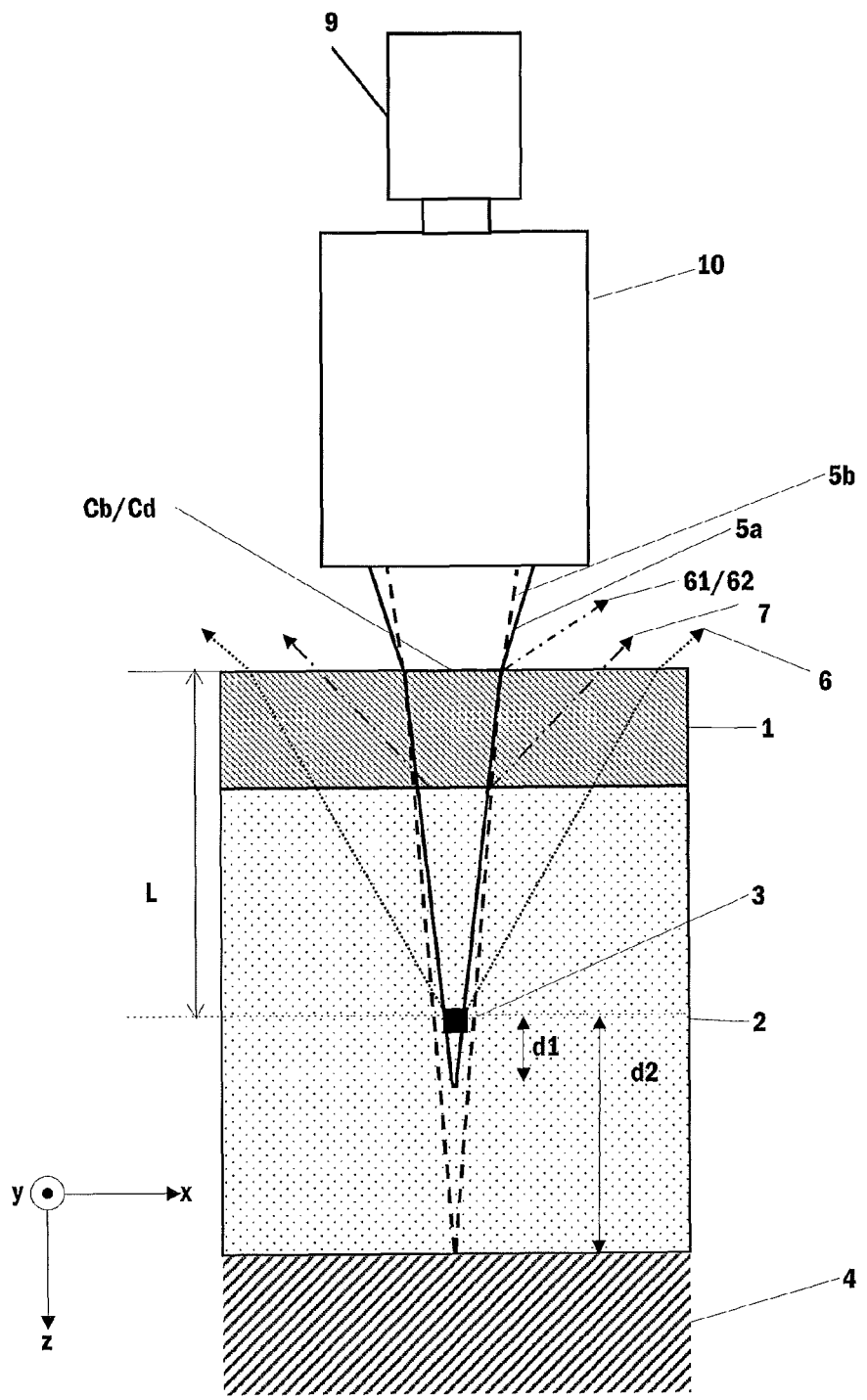
FIG. 1 shows a cross-sectional view of the skin.

A method for measuring a concentration of a biogenic substance according to an illustrative embodiment (Embodiment 1) is described with reference to the drawings. The components in the drawings are not necessarily to scale, emphasis instead being placed upon clearly illustrating the principles of the present invention. In this embodiment, a method is provided for measuring a concentration of a biogenic substance contained in a living body. The method comprises steps described in the following paragraphs:

(Step (a))

Figure 3:
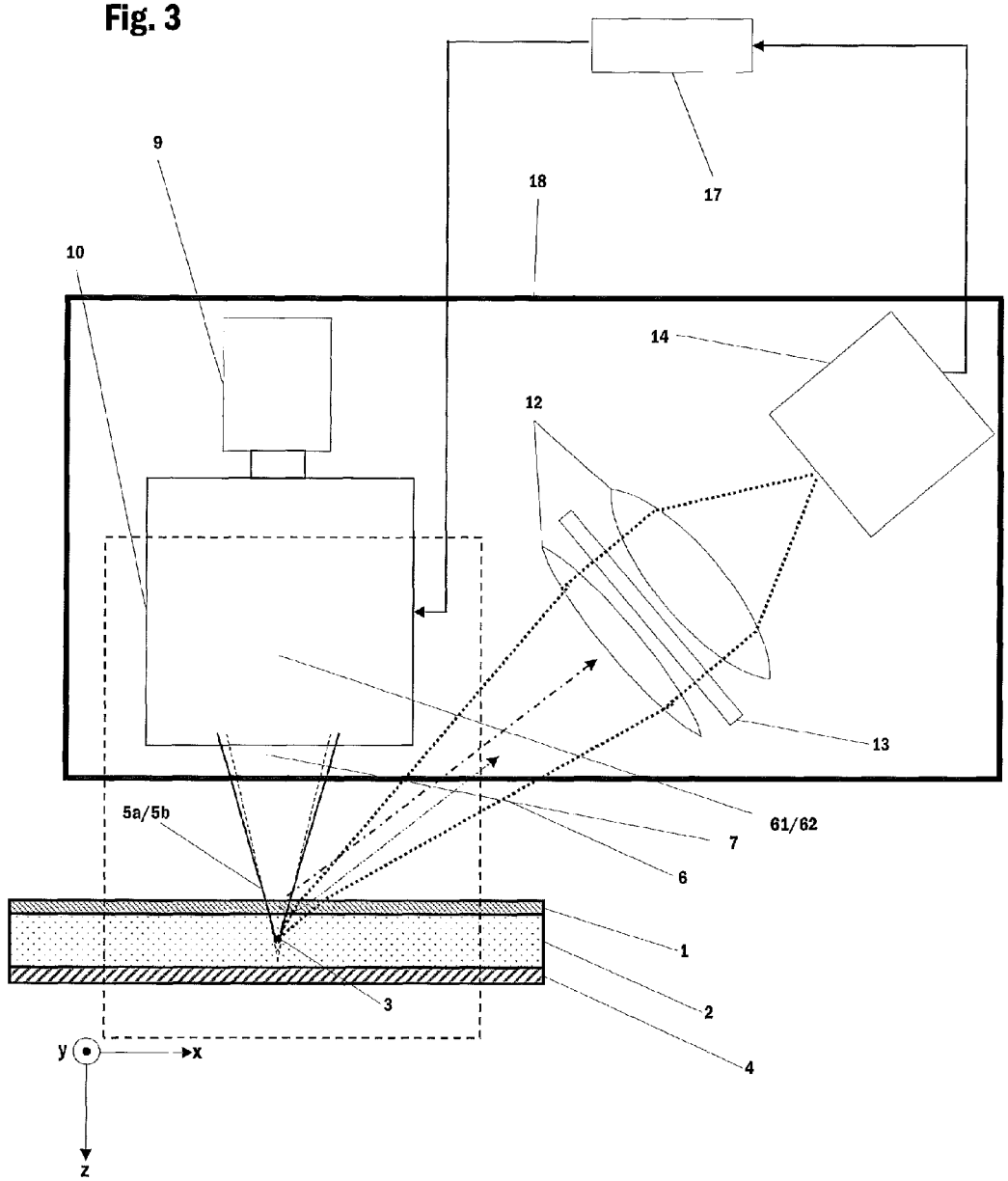
FIG. 3 shows a measuring device.

In the step (a), the measuring device is prepared. As shown in FIG. 3, the measuring device comprises a light source 9, a focusing controller 10, an optical filter 13, and a light receiver 14. The measuring device optionally comprises a lens system 12 and a computer 17.

The computer 17 calculates a concentration of the biogenic substance on the basis of the output signal of the light receiver 14. The computer 17 also controls the focusing controller 10. The support 18 holds the focusing controller 10, the lens system 12, the optical filter 13, and the light receiver 14.

(Step (b))

As shown in FIG. 1, a skin of a living body has an epidermal tissue 1, a dermal tissue 2, and a hypodermal tissue 4. The epidermal tissue 1, the dermal tissue 2, and the hypodermal tissue 4 are stacked in this order.

The epidermal tissue 1 is located at the surface of the skin. The epidermal tissue 1 has a thickness of approximately 0.2 millimeters to 0.5 millimeters. The dermal tissue 2 has a thickness of approximately 0.5 millimeters to 2 millimeters. A particle chip 3 is implanted in the dermal tissue 2 and maintained while the particle chip 3 is immersed in an interstitial fluid, which is a living fluid between tissue cells. The hypodermal tissue 4 is constituted mainly of adipose tissue.

The term "body fluid" used in the present specification means an interstitial fluid.

Since the dermal tissue 2 has a plurality of blood capillaries, the body fluid contains biogenic substances contained in the blood capillaries. In particular, because a blood capillary wall is highly permeable to glucose, glucose concentration in the body fluid has high correlativity with blood sugar level.

FIG. 1 shows an enlarged cross-sectional view of the skin surrounded by the dashed line drawn in FIG. 3. As shown in FIGS. 1-3 and FIGS. 5-12, z direction denotes the laminate direction of the skin. X direction denotes a direction orthogonal to the z direction. Y direction is the direction orthogonal to both of the z direction and the x direction.

The light source 9 transmits light along the z direction to the focusing controller 10. In the step (b), the focusing controller 10 converts this light to a first focused light 5a (depicted as a solid line in FIG. 1). The first focused light 5a is focused on the surface of the particle chip 3 through a first region Cb, which is present on the surface of the skin. Then, the first focused light 5a is reflected on the surface of the particle chip 3 to generate a first reflected light 6.

In more detail, as shown in FIG. 5, the diameter of the first focused light 5a on the surface of the particle chip 3 corresponds substantially with the diameter of the surface of the particle chip 3. As shown in FIG. 1, theoretically, the focal point of the first focused light 5a is positioned at the point left from the surface of the particle chip 3 by depth d1. As shown in FIG. 7, the focal point of the first focused light 5a may be positioned between the surface of the particle chip 3 and the surface of the skin.

(Particle Chip 3)

Figure 2:
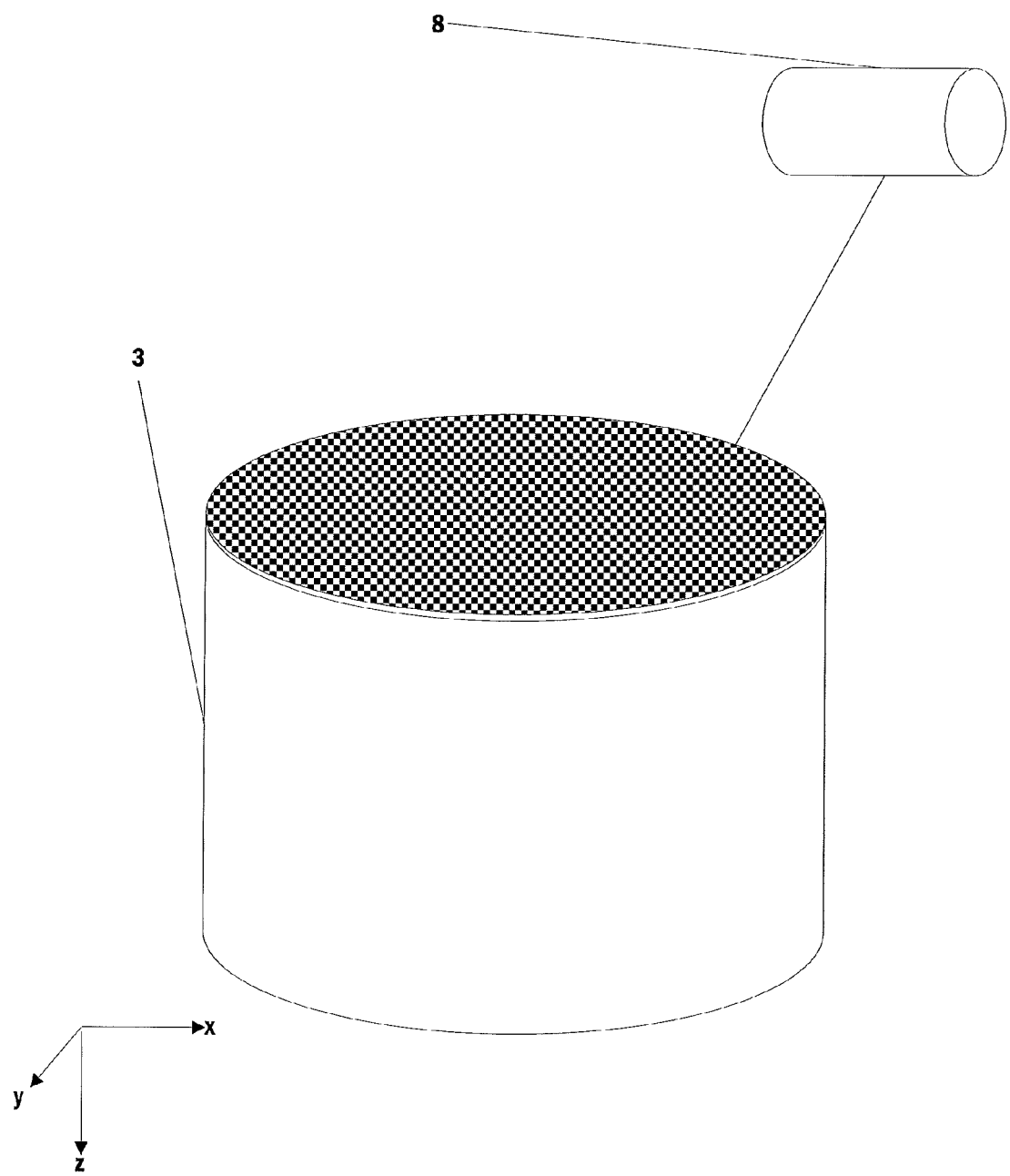
FIG. 2 shows a particle chip 3.

FIG. 2 shows an enlarged view of the particle chip 3. The particle chip 3 comprises a substrate and metal particles 8 disposed on the surface of the substrate. An example of the number of the metal particles 8 is approximately 10,000. The metal particles 8 generate localized surface plasmon resonance by being irradiated with light.

The metal particles 8 have a localized surface plasmon resonance wavelength depending on the diameter of each metal particle and on the length of each metal particle. For example, each of the metal particles 8 has a diameter of approximately 10 nanometers and a length of approximately 38 nanometers, the metal particles 8 have a localized surface plasmon resonance wavelength of 785 nanometers and a half value width of approximately 70 nm. The term "Localized surface plasmon resonance wavelength" used in the present specification means the peak wavelength of absorption of light.

As shown in FIG. 1, the particle chip 3 is implanted in the dermal tissue 2 so that the surface comprising the particles 8 is parallel to the epidermal tissue 1. The distance L from the epidermal tissue 1 to the particle chip 3 is approximately 1.5 millimeters.

Each metal particle 8 may be composed of a gold nanorod. Instead of the gold nanorod, a dielectric particle having a surface coated with metal such as gold or silver may be used. An example of the material of the dielectric particle is silica.

The substrate of the particle chip 3 has a diameter of approximately 100 micrometers and a thickness of 100 micrometers. An example of the material of the substrate is a resin such as acrylic resin, glass, and silicon. The particles 8 are disposed in such a manner that respective longitudinal axes directions are parallel to the x direction. U.S. Pre-Grant Patent application Publication No. 2010/0195106 discloses the particle chip 3 in more detail. U.S. Pre-Grant Patent application Publication No. 2010/0195106 corresponds to WO2007/108453 and Japanese patent laid-open publication No. 2007-248284.

An example of the first focused light 5a is a light having a wavelength of 785 nanometers and having a shape of a circular beam. Such a first focused light 5a penetrates the epidermal tissue 1 and is focused on the surface of the particle chip 3. When the first focused light 5a reaches the particle chip 3, the first focused light 5a is reflected on the surface of the particle chip 3 so as to generate a first reflected light 6 there.

(Step (c))

As shown in FIG. 1, the first reflected light 6 is refracted at the surface of the skin due to the difference between the refractive index of the skin (approximately 1.37) and the refractive index of air (1). Then, as shown in FIG. 3, the first reflected light 6 penetrates the optical filter 13, and the first reflected light 6 is received by the light receiver 14. Thus, a first signal Xa is obtained. It is preferable that the step (b) and the step (c) are performed at the same time.

When the particle chip 3 is irradiated with the first focused light 5a, the localized surface plasmon resonance is generated, and the electromagnetic field strength on the periphery of the particles 8 is increased. This increases the Raman scattering light from the biogenic substance located on the periphery (within the range of 0.5 to 30 nanometers) of the particles 8. Thus, surface-enhanced Raman scattering light is generated. The first reflected light 6 includes the surface-enhanced Raman scattering light.

The intensity of the surface-enhanced Raman scattering light is $10^4$ to $10^9$ times greater than the intensity of normal Raman scattering light. Accordingly, the surface-enhanced Raman scattering light generated on the periphery of the particles 8 has significantly greater intensity than the Raman scattering light generated in the skin surface (including the cuticle), in the epidermal tissue 1, or in the dermal tissue 2. This means that the Raman scattering light of a biogenic substance contained in a body fluid on the periphery of the particles 8 is selectively enhanced. Thus, the influence of the stray light and the interruption component is lowered.

The amount of the biogenic substance such as glucose contained in a living body is significantly smaller than the amount of the interruption component contained in the living body. Accordingly, normal Raman scattering light of glucose has significantly smaller intensity than the Raman scattering light of the interruption component contained in the skin surface (including the cuticle), in the epidermal tissue 1, or in the dermal tissue 2. For this reason, it is hard to extract the usual Raman scattering light of glucose.

However, the particle chip 3 selectively enhances the Raman scattering light of glucose contained in a body fluid of the dermal tissue 2. This increases the intensity of the Raman scattering light of glucose selectively, compared to the intensity of the Raman scattering light of the interruption substance. Since the intensity of the surface-enhanced Raman scattering light of glucose is proportional to the concentration of the glucose, the concentration of glucose can be calculated from the intensity of the surface-enhanced Raman scattering light of the glucose.

An example of calculating a concentration of glucose is described below.

FIG. 1 of Non Patent Literature 1 shows the surface-enhanced Raman scattering light of glucose. The surface-enhanced Raman scattering light of glucose has a plurality of peaks specific to glucose within the Raman shift range of 1000 to 1500 $cm^{-1}$.

Out of the plurality of peaks, the peak having a Raman shift of 1120 $cm^{-1}$ does not overlap the peaks of the Raman scattering light spectra of albumin and creatinine. Accordingly, the intensity of the surface-enhanced Raman scattering light having the Raman shift of 1120 $cm^{-1}$ is proportional only to the concentration of glucose.

When the wavelength of the first focused light 5a is 785 nanometers, a filter which light having a wavelength of 860.7 nanometers penetrates is used as the optical filter 13. The reason thereof is described below.

The relationship between wavelength lambda and wave number k satisfies the following equation (I):

$$k(cm^{-1}) = 10^7/\text{lambda(nanometer)} \qquad (I).$$

The wavelength of 785 nanometers corresponds to a wave number of 12,739 $cm^{-1}$. Accordingly, the wave number of the Raman scattering light specific to glucose with a Raman shift of 1120 $cm^{-1}$ is calculated by the following equation.

$$12739(cm^{-1}) - 1120(cm^{-1}) = 11619(cm^{-1}).$$

When converted according to the equation (I), the wavelength of the Raman scattering light specific to glucose, which has a Raman shift of 1120 $cm^{-1}$ is 860.7 nanometers.

For example, the optical filter 13 has a central wavelength of 860.7 nanometers and a full width at half maximum of 3 nanometers. The penetration range of the optical filter 13 is 859.2 nanometers to 862.2 nanometers. According to the equation (I), the wave number of the penetration range is 11,599 $cm^{-1}$ to 11,639 $cm^{-1}$.

Figure 4:
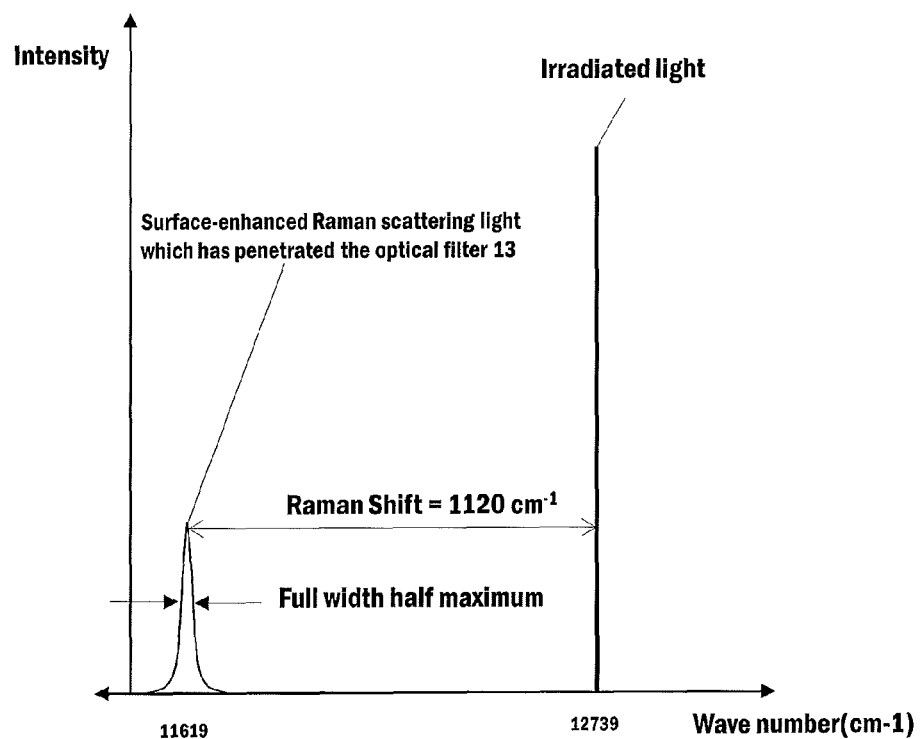
FIG. 4 is a graph showing the relationships among the irradiated light, the surface-enhanced Raman scattering light, the Raman shift, and the full width at half maximum.

FIG. 4 shows the relationships among the irradiated light, the surface-enhanced Raman scattering light, the Raman shift, and the full width at half maximum.

The central wavelength and width of the surface-enhanced Raman scattering light specific to glucose falls within the acceptable range for transmission. Which is defined by the central wavelength and width of the penetration spectrum of the optical filter 13. Because of this setting, the surface-enhanced Raman scattering light specific to glucose penetrates the optical filter 13. However, other lights fail to penetrate the optical filter 13.

In more detail, as shown in FIG. 4, only the Raman scattering light having a Raman shift value ranging from 1100 $cm^{-1}$ to 1140 $cm^{-1}$ with regard to the first focused light 5a, which has a wave number of 12,739 $cm^{-1}$, penetrates the optical filter 13 selectively. On the other hand, the optical filter 13 selectively restricts transmission of unwanted wavelengths of light, which includes the Raman scattering light of the interruption component and the first reflected light 6. The wave number of the Raman shift light having a Raman shift of 1100 $cm^{-1}$ is 11,639 $cm^{-1}$ (12,739 $cm^{-1}$ − 1,100 $cm^{-1}$ = 11,639 $cm^{-1}$), and the wave number of the Raman shift light having a Raman shift of 1140 $cm^{-1}$ is 11,599 $cm^{-1}$. (12,739 $cm^{-1}$ − 1,140 $cm^{-1}$ = 11,599 $cm^{-1}$.). These values correspond with the wave numbers of the end points of the penetration range of the optical filter 13.

If the intensity of the first focused light 5a is enhanced in order to enhance the intensity of the surface enhanced Raman scattered light, the intensity of the reflected light 6 and the intensity of the Raman scattered light of interruption components are also enhanced. However, the Raman scattered light of the interruption components and the reflected light 6 components are shielded by the optical filter 13, and do not reach the light sensor 14. Thus, only the first signal Xa specific to the target substance is obtained.

The central wavelength $lambda_2$ of the optical filter 13 used for measuring a glucose concentration is calculated by the following formula (II). $Lambda_1$ represents a wavelength of the first focused light 5a.

$$lambda_2 = (10^7 * lambda_1)/(10^7 - 1120 * lambda_1) \qquad (II)$$

$lambda_2$: the central wavelength of the optical filter 13
$lambda_1$: the wavelength of the first focused light 5a

As described above, the measuring device is used to selectively measure the surface-enhanced Raman scattering light of glucose, which has the Raman shift of 1120 $cm^{-1}$.

Needless to say, similarly to a case of a typical measurement, a standard curve prepared beforehand is used on the above-mentioned measurement.

Instead of the equation (II), the following equation (III) is employed to calculate a concentration of a biogenic substance having a Raman shift of B $cm^{-1}$:

$$lambda_2 = (10^7 * lambda_1)/(10^7 - B * lambda_1) \qquad (III)$$

$lambda_2$: the central wavelength of the optical filter 13
$lambda_1$: the wavelength of the first focused light 5a
B: Raman shift of the biogenic substance
(Steps (d) to (f))

Seemingly, the concentration of the biogenic substance is believed to be measured through the step (a) to the step (c). However, the obtained value of the concentration is inaccurate. The reason is described below.

The stray light lowers the measurement accuracy. The stray light includes a first reflected stray light 61 and the diffused and scattered light 7. The first reflected stray light 61 is generated from the skin surface by irradiating the skin surface with the first focused light 5a. The diffused and scattered light 7 is generated from the inside of the skin by the focused light 5a travelling inside of the skin.

The first reflected stray light 61 lowers the measurement accuracy largely, whereas the diffused and scattered light 7 hardly lowers the measurement accuracy. This is because the intensity of the first reflected stray light 61 is much greater than the intensity of the diffused and scattered light 7.

The larger the difference of the refractive index is, the greater the amount of the first reflected stray light 61 is. The first focused light 5a travels from air to the inside of the skin. Due to the large difference, which is approximately 0.37, between the refractive index of air and the refractive index of the skin, the first focused light 5a is largely reflected at the skin surface.

On the other hand, since the refractive index of the inside of the skin (approximately 1.37) is substantially constant, the intensity of the diffused and scattered light 7 is much weaker than that of the first reflected stray light 61. Accordingly, the diffused and scattered light 7 is omitted below.

The first focused light 5a is reflected strongly to all directions on the skin surface to generate the first reflected stray light 61. The first reflected stray light 61 is generated at the cuticle, which has a thickness of 10 micrometers to 20 micrometers and is located at the forefront of a skin. The intensity of the first reflected stray light 61 is equal to approximately four to seven percent of the intensity of the irradiated light. The intensity of the first reflected stray light 61 varies depending on the surface roughness of the cuticle and on the distribution of the areas each having different refractive index.

On the other hand, the intensity of normal Raman scattering light is not more than $10^{-16}$ times than the intensity of the irradiated light. And the intensity of the surface-enhanced Raman scattering light is not more than $10^{-7}$ times than the intensity of the irradiated light. Namely, the intensity of the first reflected stray light 61 generated on the skin surface is significantly greater than that of the surface-enhanced Raman scattering light, which should be detected. Accordingly, even if the intensity of the first reflected stray light 61 is significantly small, incorporation of the first reflected stray light 61 into the light receiver 14 saturates the output signal of the light receiver 14 and causes the measurement to be impossible.

The optical filter 13 may decrease the amount of the first reflected stray light 61 incorporating into the light receiver 14 and may prevent the light sensor 14 from being saturated.

However, when the transmittance of the light penetrating the optical filter 13 is decreased (namely, when the shielding effect of the optical filter 13 is increased), the transmittance of the Raman scattering light is also decreased. Practically, the minimum value of the transmittance of the light penetrating the optical filter 13 is approximately $10^{-8}$. Namely, all the first reflected stray light 61 is not shielded, and some of the first reflected stray light 61 penetrates the optical filter 13. The some of the first reflected stray light 61 incorporates into the light receiver 14, and lowers the measurement accuracy of the concentration of the biogenic substance.

Furthermore, living bodies have substances having a Raman spectrum which overlaps the Raman spectrum of the biogenic substance such as glucose. Even if the optical filter 13 is used, the Raman scattering light (hereinafter, "the interruption Raman light") generated by the substances fails to be decreased. This also lowers the measurement accuracy of the concentration of the biogenic substance.

In order to solve the above-mentioned problem, the steps (d) to (f) are performed in this embodiment of the present invention. It is preferred that the step (d) and the step (e) are performed at the same time. It is more preferred that the steps (d) to (f) are performed at the same time.

(Step (d))

First, in the step (d), the focusing controller 10 converts the light transmitted from the light source 9 to a second focused light 5b (depicted as a dashed line in FIG. 1) in such a manner that an inequation: d1<d2 is satisfied. Here, distances d1 and d2 represent a distance (a depth) between the focal point of the second focused light 5b and the surface of the particle chip 3, and a distance (a depth) between the focal point of the second focused light 5b and the surface of the particle chip 3, respectively.

As shown in FIG. 1, the second focused light 5b penetrates a second area Cd, and reaches the surface of the particle chip 3. The second focused light 5b generates a second reflection light there.

As shown in FIG. 6 (and FIG. 5), the second focused light 5b has a larger beam diameter on the surface of the particle chip 3 than the first focused light 5a. As is clear from the comparison of FIG. 5 to FIG. 6, the second focused light 5b has a smaller intensity on the surface of the particle chip 3 than the first focused light 5a.

As long as the focal points of the first focus light 5a and the second focus light 5b is different, the inequation: d1<d2 does not always have to be satisfied. Similar to the case of the first focused light 5a shown in FIG. 7, the focal point of the second focused light 5b may be positioned between the surface of the particle chip 3 and the surface of the skin, as shown in FIG. 8.

Figure 9:
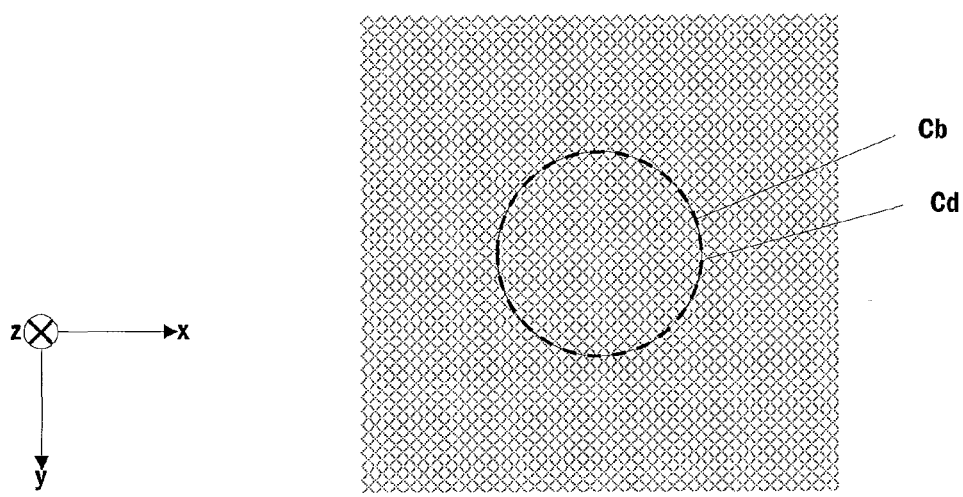
FIG. 9 shows a first area Cb and a second area Cd.

As shown in FIG. 9, it is necessary that the first area Cb and the second area Cd are the same. This reason is described below.

Optical characteristic depends on surface roughness, distribution of the refractive index, and the concentration of the interruption component. The optical characteristic is not uniform even in a single individual. Namely, the optical characteristic varies depending on the position on the skin surface. Accordingly, even if a single individual is irradiated with the light having identical intensity, the intensity of the first reflected stray light 61 varies depending on the position which is irradiated with the light. For this reason, it is necessary that the first area Cb and the second area Cd are the same, as shown in FIG. 9.

Similarly to the case of the step (b), reflected stray light is also generated in the step (d). The reflected stray light generated in the step (d) is referred to as the second reflected stray light 62.

(Steps (e) and (f))

Similarly to the case of the step (c), in the step (e), the second reflected stray light 62 is received by the light receiver 14 through the optical filter 13 to obtain a second signal Xb. Finally, in the step (f), the second signal Xb is deducted from the first signal Xa to calculate the difference therebetween. The concentration of the biogenic substance is calculated on the basis of the difference by the computer 17.

The deduction of the second signal Xb from the first signal Xa cancels the first reflected stray light 61, which lowers the measurement accuracy greatly. The interruption Raman light is also cancelled. Namely, the difference includes the component of neither the first reflected stray light 61 nor the interruption Raman light. Accordingly, the concentration obtained through the steps (a) to (f) is more accurate than the concentration obtained through only the steps (a) to (c).

Figure 10:
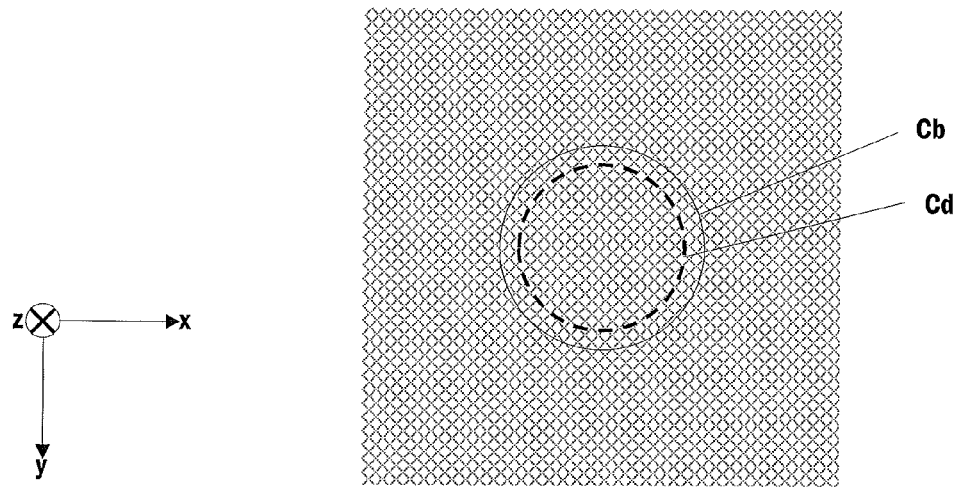
FIG. 10 shows the first area Cb and the second area Cd.
Figure 11:
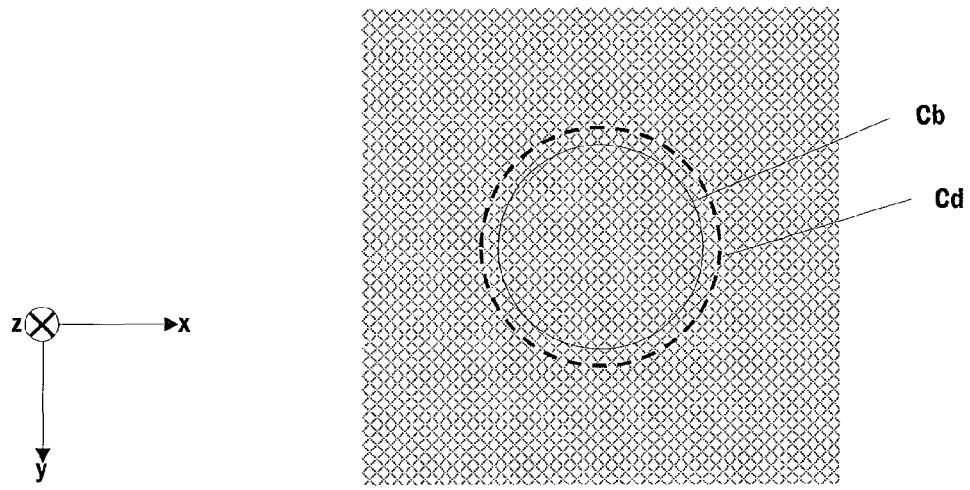
FIG. 11 shows the first area Cb and the second area Cd.

As shown in FIGS. 10 and 11, the first area Cb and the second area Cd must not be different. Since the first reflected stray light 61 is not cancelled insufficiently by the second reflected stray light 62 or the second reflected stray light 62 cancels the first reflected stray light 61 beyond necessity, the difference in the step (f) includes either of the first or second reflected stray light. The concentration of the biogenic substance based on the difference is inaccurate.

Figure 12:
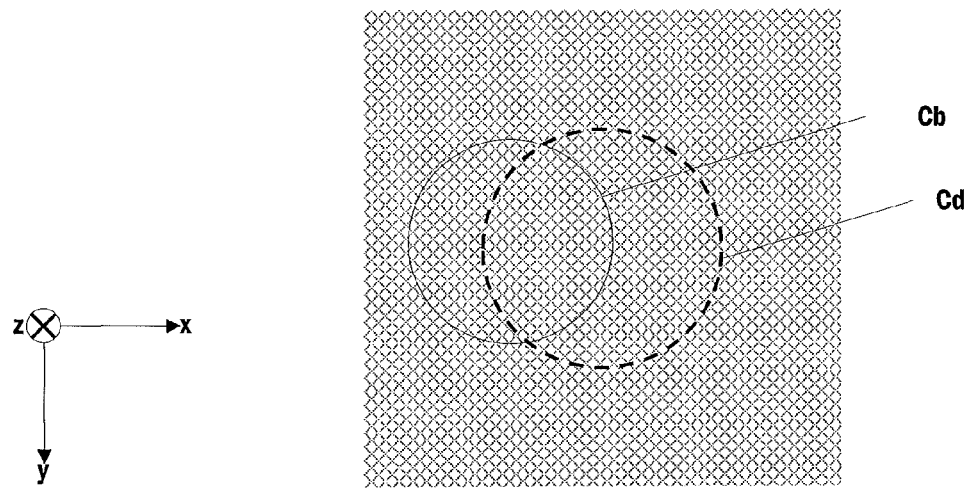
FIG. 12 shows the first area Cb and the second area Cd.

As shown in FIG. 12, it is insufficient that the first area Cb corresponds with the second area Cd partially. Accordingly, as shown in FIG. 9, the median point of the first area Cb corresponds with the median point of the second area Cd, and the first area Cb is congruent to the second area Cd. When both of the first area Cb and the second area Cd are circular, these median points correspond with the center point of the circle.

INDUSTRIAL APPLICABILITY

The present invention can be employed to measure the concentration of the biogenic substance such as glucose in a living body.

REFERENTIAL SIGNS LIST

1: epidermal tissue
2: dermal tissue
3: particle chip
4: hypodermal tissue
5$a$: first focused light
5$b$: second focused light
6: reflected light
61: first reflected stray light
62: second reflected stray light
7: diffused and scattered light
8: metal particles
9: light source
10: focusing controller
12: Lens system
13: optical filter
14: light receiver
17: computer
18: support
Cb: first area
Cd: second area

The invention claimed is:

1. A method for measuring a concentration of a biogenic substance contained in a living body, the method comprising steps of:

a step (a) of preparing a measuring device comprising a light source, a focusing controller, an optical filter, and a light receiver;

a step (b) of transmitting a first focused light from the light source through the focusing controller, and focusing the first focused light on a surface of a particle chip implanted in a skin though a first area on the surface of the skin so as to generate a first reflected light, wherein the particle chip comprises a substrate and a plurality of metal particles, a step (c) of receiving the first reflected light by the light receiver through the optical filter to obtain a first signal Xa, the following equation (III) is satisfied:

$$\text{lambda}_2 = (10^7 \ast \text{lambda}_1)/(10^7 - B \ast \text{lambda}_1) \quad \text{(III)},$$

lambda$_2$: the central wavelength of optical filter,
lambda$_1$: the wavelength of the first focused light,
B: Raman shift of the biogenic substance;

a step (d) of transmitting a second focused light from the light source through the focusing controller, and irradiating the surface of the particle chip with the second focused light through a second area on the surface of the skin so as to generate a second reflected light, wherein the focal point of the second focused light is different from the focal point of the first focused light, the first area is identical to the second area, and a step (e) of receiving the second reflected light by the light receiver through the optical filter to obtain a second signal Xb, a step (f) of calculating the concentration of the biogenic substance on the basis of the difference between the first signal Xa and the second signal Xb.

2. A method according to claim 1, wherein,
the biogenic substance is glucose, and
B is 1120 cm$^{-1}$.

3. A method according to claim 1, wherein,
the steps (b) and (c) are performed at the same time.

4. A method according to claim 1, wherein,
the steps (d) and (e) are performed at the same time.

5. A method according to claim 1, wherein,
the steps (d) to (f) are performed at the same time.

* * * * *